United States Patent
Raycheck et al.

(10) Patent No.: US 8,939,957 B2
(45) Date of Patent: Jan. 27, 2015

(54) ABSORBENT ARTICLE WITH LEG GASKETING CUFF

(75) Inventors: Jeromy Thomas Raycheck, South Lebanon, OH (US); Lisa Jane Goodlander, Okeana, OH (US); Lisa Maria Grinkemeyer, Harrison, OH (US); Jessica Lee Mosman, Cincinnati, OH (US); Jason Edward Naylor, Loveland, OH (US); LeAnne Nichole Phillips, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 428 days.

(21) Appl. No.: 13/457,521

(22) Filed: Apr. 27, 2012

(65) Prior Publication Data

US 2012/0277713 A1   Nov. 1, 2012

Related U.S. Application Data

(60) Provisional application No. 61/480,663, filed on Apr. 29, 2011.

(51) Int. Cl.
*A61F 13/15* (2006.01)
(52) U.S. Cl.
USPC ............ 604/385.28; 604/385.24; 604/385.25; 604/385.26; 604/385.27; 604/385.29
(58) Field of Classification Search
USPC ............ 604/385.28, 385.24, 385.25, 385.26, 604/385.27, 385.29
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 4,610,678 A | 9/1986 | Weisman et al. |
| 4,662,875 A | 5/1987 | Hirotsu et al. |
| 4,673,402 A | 6/1987 | Weisman et al. |
| 4,699,622 A | 10/1987 | Toussant et al. |
| 4,808,178 A | 2/1989 | Aziz et al. |
| 4,834,735 A | 5/1989 | Alemany et al. |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |

(Continued)

FOREIGN PATENT DOCUMENTS

| | | |
|---|---|---|
| EP | 0 403 832 B1 | 10/1994 |
| JP | 2000-342623 | 12/2000 |

(Continued)

OTHER PUBLICATIONS

PCT International Search Report mailed Oct. 26, 2012 (15 pages).

*Primary Examiner* — Jacqueline F. Stephens
(74) *Attorney, Agent, or Firm* — Andrew J. Mueller; Laura L. Whitmer

(57) ABSTRACT

A disposable absorbent article may include a topsheet, a backsheet, an absorbent core disposed between the topsheet and the backsheet, and a leg gasketing system. The leg gasketing system may include an inner cuff and an outer cuff; the inner cuff may include an inner cuff folded edge and an inner cuff material edge and the outer cuff may include an outer cuff folded edge and an outer cuff material edge such that the web of material is folded laterally inward to form the outer cuff folded edge and folded laterally outward to form the inner cuff material edge.

32 Claims, 8 Drawing Sheets

(56) References Cited

U.S. PATENT DOCUMENTS

| | | |
|---|---|---|
| 4,946,527 A | 8/1990 | Battrell |
| 4,963,140 A | 10/1990 | Robertson et al. |
| 4,990,147 A | 2/1991 | Freeland |
| 5,021,051 A | 6/1991 | Hiuke |
| 5,037,416 A | 8/1991 | Allen et al. |
| 5,061,261 A | 10/1991 | Suzuki et al. |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,171,391 A | 12/1992 | Chmielewski et al. |
| 5,221,274 A | 6/1993 | Buell et al. |
| 5,242,436 A | 9/1993 | Weil et al. |
| 5,260,345 A | 11/1993 | Desmarais et al. |
| 5,269,775 A | 12/1993 | Freeland et al. |
| 5,281,207 A | 1/1994 | Chmielewski et al. |
| 5,342,338 A | 8/1994 | Roe |
| 5,387,207 A | 2/1995 | Dyer et al. |
| 5,397,316 A | 3/1995 | Lavon et al. |
| 5,499,978 A | 3/1996 | Buell et al. |
| 5,507,736 A | 4/1996 | Clear et al. |
| 5,554,145 A | 9/1996 | Roe et al. |
| 5,569,234 A | 10/1996 | Buell et al. |
| 5,571,096 A | 11/1996 | Dobrin et al. |
| 5,575,785 A | 11/1996 | Gryskiewicz et al. |
| 5,580,411 A | 12/1996 | Nease et al. |
| 5,584,828 A | 12/1996 | Yamamoto et al. |
| 5,591,152 A | 1/1997 | Buell et al. |
| 5,607,760 A | 3/1997 | Roc |
| 5,609,587 A | 3/1997 | Roe |
| 5,625,222 A | 4/1997 | Yoneda et al. |
| 5,635,191 A | 6/1997 | Roe et al. |
| 5,643,243 A | 7/1997 | Klemp |
| 5,643,588 A | 7/1997 | Roe et al. |
| 5,672,166 A | 9/1997 | Vandemoortele |
| 5,674,215 A | 10/1997 | Ronnberg |
| 5,827,259 A | 10/1998 | Laux et al. |
| 5,827,387 A | 10/1998 | Reynolds et al. |
| 5,865,823 A | 2/1999 | Curro |
| 5,879,341 A | 3/1999 | Odorzynski et al. |
| 5,895,382 A | 4/1999 | Popp et al. |
| 5,904,675 A | 5/1999 | Laux et al. |
| 5,911,713 A | 6/1999 | Yamada et al. |
| 5,931,825 A | 8/1999 | Kuen et al. |
| 5,931,826 A | 8/1999 | Faulks et al. |
| 5,993,433 A | 11/1999 | St. Louis et al. |
| 6,004,306 A | 12/1999 | Roe et al. |
| 6,107,537 A | 8/2000 | Elder et al. |
| 6,117,121 A | 9/2000 | Faluks et al. |
| 6,120,486 A | 9/2000 | Toyoda et al. |
| 6,120,487 A | 9/2000 | Ashton |
| 6,123,694 A | 9/2000 | Pieniak et al. |
| 6,171,290 B1 | 1/2001 | Boisse et al. |
| 6,174,302 B1 | 1/2001 | Kumasaka |
| 6,186,996 B1 | 2/2001 | Martin |
| 6,248,097 B1 | 6/2001 | Beitz et al. |
| 6,264,642 B1 | 7/2001 | Kuen et al. |
| 6,293,934 B1 | 9/2001 | Kumasaka |
| 6,346,162 B1 | 2/2002 | Reynolds et al. |
| 6,413,249 B1 | 7/2002 | Turi et al. |
| 6,432,098 B1 | 8/2002 | Kline et al. |
| 6,440,117 B1 | 8/2002 | Itoh et al. |
| 6,451,001 B2 | 9/2002 | Kumasaka |
| 6,461,342 B2 * | 10/2002 | Tanji et al. ............... 604/385.25 |
| 6,494,872 B1 | 12/2002 | Suzuki et al. |
| 6,527,893 B1 | 3/2003 | Boisse et al. |
| 6,569,139 B1 | 5/2003 | Datta et al. |
| 6,569,140 B1 | 5/2003 | Mizutani et al. |
| 6,592,562 B2 | 7/2003 | Menard et al. |
| 6,613,033 B1 | 9/2003 | Popp et al. |
| 6,629,967 B1 | 10/2003 | Simmons et al. |
| 6,638,262 B2 | 10/2003 | Suzuki et al. |
| 6,641,692 B2 | 11/2003 | Reynolds et al. |
| 6,659,990 B1 | 12/2003 | Odorzynski et al. |
| 6,682,515 B1 | 1/2004 | Mizutani et al. |
| 6,682,516 B2 | 1/2004 | Johnston et al. |
| 6,699,228 B1 | 3/2004 | Chmielewski et al. |
| 6,706,029 B1 | 3/2004 | Suzuki et al. |
| 6,706,030 B1 | 3/2004 | Okuda et al. |
| 6,767,343 B2 | 7/2004 | Shimada et al. |
| 6,978,486 B2 | 12/2005 | Zhou et al. |
| 7,150,729 B2 | 12/2006 | Shimada et al. |
| 7,163,530 B1 | 1/2007 | Toyoshima et al. |
| 7,169,136 B2 | 1/2007 | Otsubo et al. |
| 7,189,219 B1 | 3/2007 | Kasai et al. |
| 7,207,978 B2 | 4/2007 | Takino et al. |
| 7,226,437 B2 | 6/2007 | Sasaki et al. |
| 7,338,479 B2 | 3/2008 | Fujioka et al. |
| 7,435,243 B2 | 10/2008 | Miyamoto |
| 7,435,244 B2 | 10/2008 | Schroer et al. |
| 7,527,616 B2 | 5/2009 | Miyamoto |
| 7,561,602 B1 | 7/2009 | Nakabayashi |
| 7,604,625 B2 | 10/2009 | Turi et al. |
| 7,621,900 B2 | 11/2009 | Van Gompel et al. |
| 7,666,176 B2 | 2/2010 | Erdman et al. |
| 7,670,325 B2 | 3/2010 | Sugiyama et al. |
| 7,708,725 B2 | 5/2010 | Kinoshita et al. |
| 7,727,214 B2 | 6/2010 | Torigoshi et al. |
| 7,753,899 B2 | 7/2010 | Mori et al. |
| 7,785,309 B2 | 8/2010 | Van Gompel et al. |
| 7,794,441 B2 | 9/2010 | Ashton et al. |
| 7,918,839 B2 | 4/2011 | Ehrnsperger et al. |
| 7,918,840 B2 | 4/2011 | Corneliusson |
| 8,002,760 B2 | 8/2011 | Ehrnsperger et al. |
| 8,043,275 B2 | 10/2011 | Peterson |
| 8,062,279 B2 | 11/2011 | Miyamoto |
| 8,075,543 B2 | 12/2011 | Okuda |
| 8,114,059 B2 | 2/2012 | Ehrnsperger et al. |
| 8,328,782 B2 | 12/2012 | Catalan et al. |
| 8,513,483 B2 | 8/2013 | Tee et al. |
| 8,679,084 B2 | 3/2014 | Kurihara |
| 8,795,250 B2 | 8/2014 | O'Connell |
| 2004/0002690 A1 | 1/2004 | Miyamoto |
| 2005/0095700 A1 | 5/2005 | Budzowski et al. |
| 2005/0113790 A1 | 5/2005 | Suzuki |
| 2005/0177123 A1 | 8/2005 | Catalan |
| 2005/0288645 A1 * | 12/2005 | LaVon ............... 604/385.21 |
| 2006/0264860 A1 * | 11/2006 | Beck et al. ............ 604/385.101 |
| 2007/0073259 A1 | 3/2007 | Erdman et al. |
| 2007/0287983 A1 * | 12/2007 | Lodge et al. ............... 604/402 |
| 2008/0077111 A1 | 3/2008 | Erdman et al. |
| 2008/0195071 A1 | 8/2008 | Ponomarenko et al. |
| 2010/0305532 A1 | 12/2010 | Ashton et al. |
| 2011/0066128 A1 | 3/2011 | Takahashi |
| 2011/0196327 A1 * | 8/2011 | Chhabra et al. ............... 604/367 |
| 2012/0277702 A1 | 11/2012 | Raycheck et al. |
| 2012/0277713 A1 | 11/2012 | Raycheck et al. |

FOREIGN PATENT DOCUMENTS

| | | |
|---|---|---|
| WO | WO 95/16746 A1 | 6/1995 |
| WO | WO 97-20532 A1 | 6/1997 |
| WO | WO 2005/095700 A1 | 10/2005 |

* cited by examiner

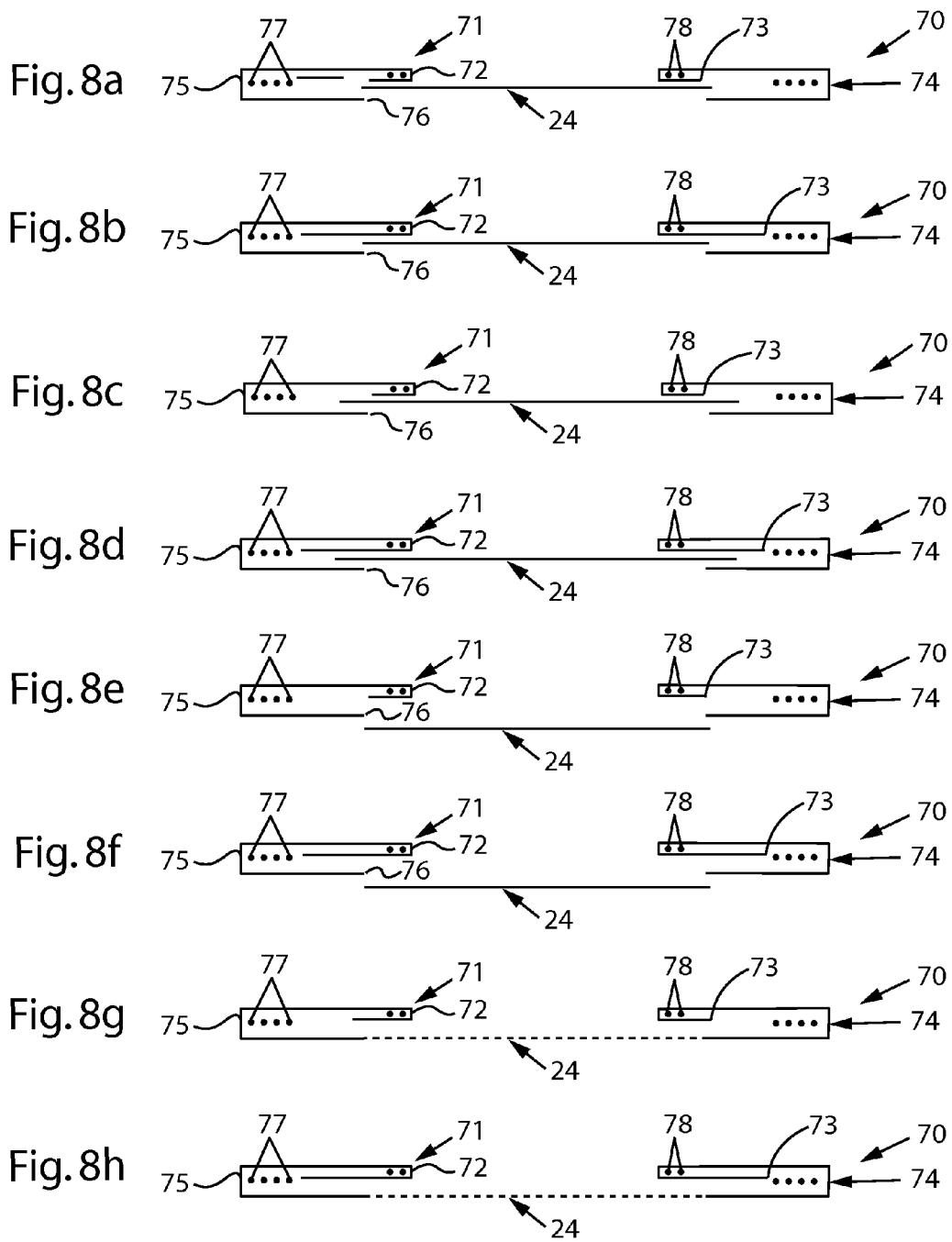

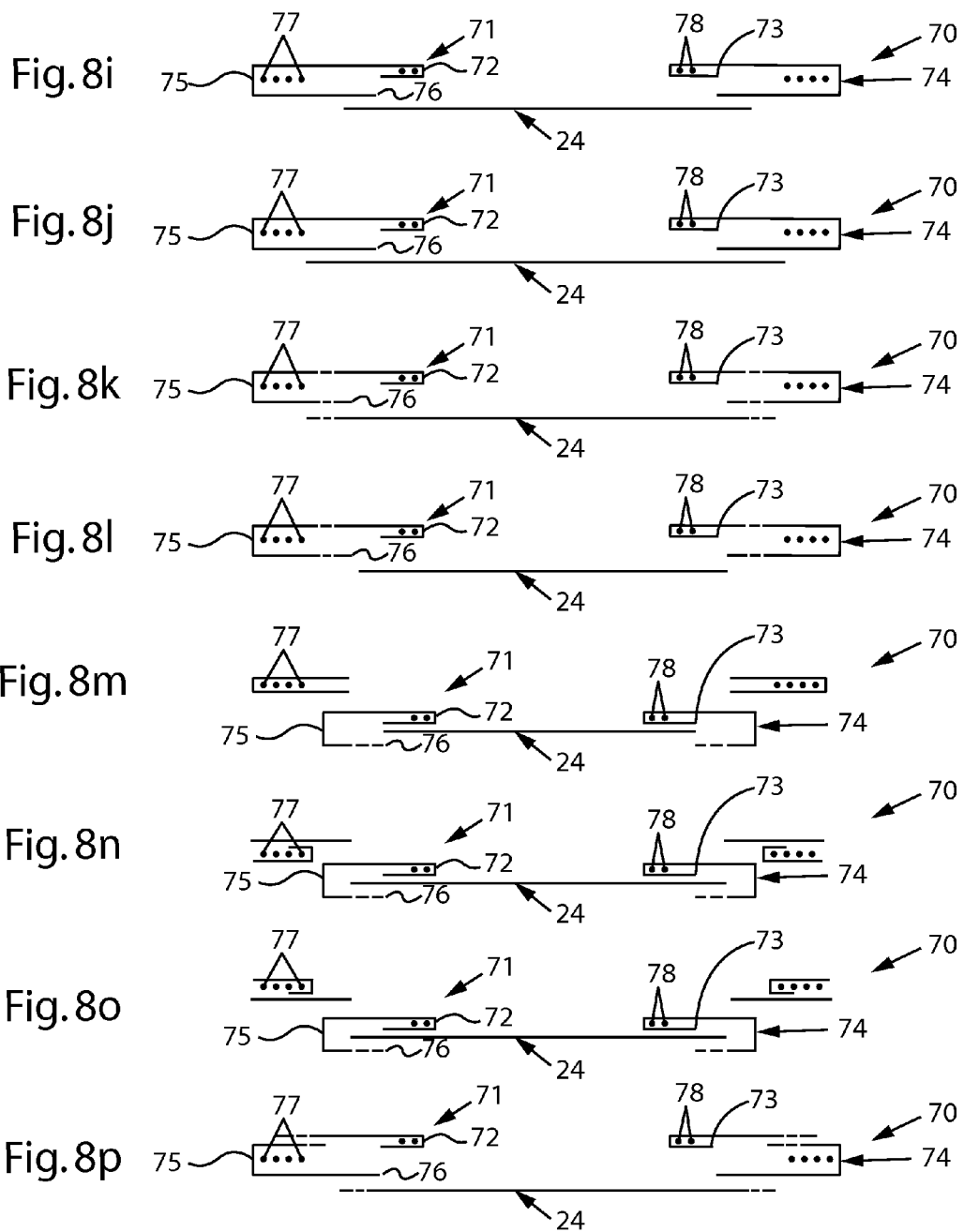

ABSORBENT ARTICLE WITH LEG GASKETING CUFF

CROSS REFERENCE TO RELATED APPLICATION

This application claims the benefit of U.S. Provisional Application No. 61/480,663, filed Apr. 29, 2011, which is herein incorporated by reference in its entirety.

FIELD OF INVENTION

This invention relates to absorbent articles such as diapers having improved leg cuffs that yield a more garment-like article. The absorbent article may have improved functional characteristics and communicative properties.

BACKGROUND OF THE INVENTION

It has long been known that absorbent articles such as conventional taped diapers offer the benefit of receiving and containing urine and/or other bodily exudates. To effectively contain exudates, the article should provide a snug fit around the waist and legs of a wearer. Absorbent articles are known to have a chassis comprising a topsheet, a backsheet, and an absorbent core.

Current diaper designs frequently include the use of an inner barrier leg cuff to prevent leakage of bodily exudates and an outer leg cuff which provides a covering over the inner leg cuff to minimize the visibility of exudates through the inner cuff and provide a secondary means to capture bodily exudates should they breach the inner barrier leg cuff. The inner barrier leg cuff may be made using a hydrophobic nonwoven and may be disposed on the body-facing surface of the absorbent article or connected to the body-facing surface of the film backsheet layer. The inner barrier leg cuff may be a substantially liquid impervious layer that prevents bodily exudates from passing out of the sides of the article and may also be highly breathable, allowing outside air to reach the skin to help maintain a healthy level of skin hydration. In many current diapers, the outer leg cuff comprises the polymeric film layer of the backsheet to provide high opacity required to cover the inner leg cuff as well as to prevent molten adhesive from passing through the cuff to the garment-facing surface of the article during manufacturing. The outer leg cuff contains the outer leg elastic strands, which create the contraction forces and gathers, and can be sandwiched between the cuff material and backsheet material. The elastic strands in the leg cuffs are typically joined with molten adhesive during manufacture, and the hot adhesive generally has the potential to pass through nonwoven materials during manufacture, causing contamination of manufacturing lines as well as the potential for stickiness on the outside surface of the article. The polymeric film generally is used to prevent these issues, however, results in a plastic-like look as well as a noisy application process.

Because of manufacturing tolerances when cutting, tracking, and combining materials, the outer leg elastic strands are generally spaced inboard from the longitudinal edge of the article in the crotch region. This prevents inadvertent cutting or exposure of the outer leg elastic strands during the manufacturing process. This design does not result in the outermost portion of the longitudinal edge of the product continuously contacting closely to the skin of the user during wear. Thus, the ability of the elastic strand(s) to control the edge of the article diminishes as the distance between the outermost elastic and the edge increases, leading to a more random distribution of larger gathers which contact the skin at larger intervals or sometimes not at all. This effect can lead to user perception that the diaper may leak where the longitudinal edge does not contact the skin of the user. In addition, many articles currently available contain only two to three outer leg elastics per side to create the gathers, increasing the difficulty of achieving the desired appearance of a wide finished leg cuff or more garment-like cuff such as the elasticized hemmed edge of the arm cuff of a sweater. If the elastics are spaced more closely, the result is a narrow section of elasticized zone, which results in a less finished, less comfortable, and less clothing-like appearance. If the elastics are spaced farther apart, the gathers can appear to separate further from the skin of the user, leading to a perception of potential leakage risk. As discussed above, this is driven by having less control of the gathers between strands of increasing separation.

Accordingly, it is desirable to provide a folded outer leg cuff design having finished edges with elastics that are close to the edge to maintain a close proximity to the skin to create improved fit, a more aesthetically pleasing, clothing-like design and improved leakage protection. It is also desirable that the article have a folded outer leg cuff design that does not have a polymeric film in the elasticized region and still prevents penetration of exudates and molten adhesive.

SUMMARY OF THE INVENTION

The present invention relates to a disposable absorbent article that comprises a first waist region, a second waist region, a crotch region between the first and second waist regions, a first waist edge, a second waist edge, a first longitudinal edge, and a second longitudinal edge. The absorbent article comprises a topsheet, a backsheet, an absorbent core disposed between the topsheet and the backsheet, and a leg gasketing system. The leg gasketing system may comprise one web or multiples webs of material.

The leg gasketing system may comprise both an inner cuff and an outer cuff. The inner cuff of the leg gasketing system may comprise an inner cuff folded edge and an inner cuff material edge. The outer cuff may comprise an outer cuff folded edge and an outer cuff material edge such that the web of material is folded laterally inward to form the outer cuff folded edge and folded laterally outward to form the inner cuff material edge. The leg gasketing system may extend from the first waist edge to the second waist edge may be joined to the topsheet and/or backsheet, or other layers in between the inner cuff folded edge and the outer cuff folded edge in the crotch region. In one embodiment, the folded outer leg cuff web of material does not comprise a polymeric film. In one embodiment, the folded outer leg cuff web of material comprises an N-fiber material.

DETAILED DESCRIPTION OF THE INVENTION

Figure 1:
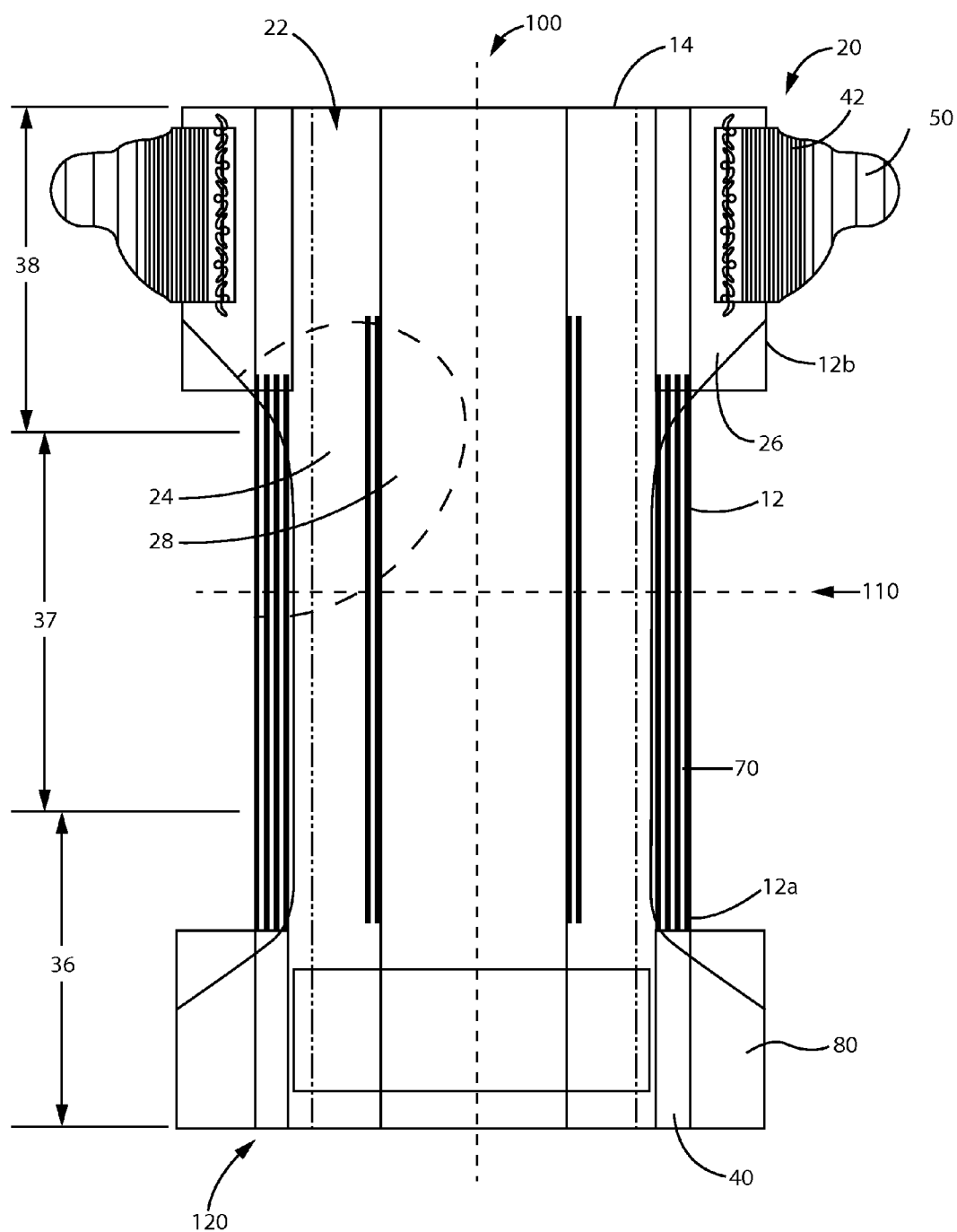
FIG. 1 is a plan view of an exemplary diaper.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

"Pant" refers to disposable absorbent articles having a preformed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

The present invention is directed to a leg gasketing system that comprises a folded outer leg cuff having neatly finished outer cuff folded edges that creates an aesthetically pleasing design that is garment like. In one embodiment, the folded outer leg cuff design is advantageous in preventing penetration and adhesive bleedthrough without the use of a polymeric film layer in the elasticized region. In one embodiment, the absorbent article may comprise an opacity strengthening patch to provide the strength needed to prevent the article from extending excessively during application and wearing, and provide the opacity at the sides and waist to prevent the skin of the user from showing through the article.

FIG. 1 is a plan view of an exemplary, non-limiting embodiment of an absorbent article 20 of the present invention in a flat, uncontracted state (i.e., without elastic induced contraction). The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic elements such that they gather about the waist of the wearer to provide improved fit and containment. The crotch region 37 is that portion of the absorbent article 20 which, when the absorbent article 20 is worn, is generally positioned between the legs of the wearer.

The outer periphery of chassis 22 is defined by longitudinal edges 12 and lateral edges 14. The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprise a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the absorbent article 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U.

Any portion of the topsheet 24 may be coated with a lotion or skin care composition as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores are described in greater details below.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537.

Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12. The integral ear may be formed by cutting the chassis form to include the shape of the ear projection.

The absorbent article 20 may also include a fastening system 50. When fastened, the fastening system 50 interconnects the first waist region 36 and the rear waist region 38 resulting in a waist circumference that may encircle the wearer during wear of the absorbent article 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

Figure 2:
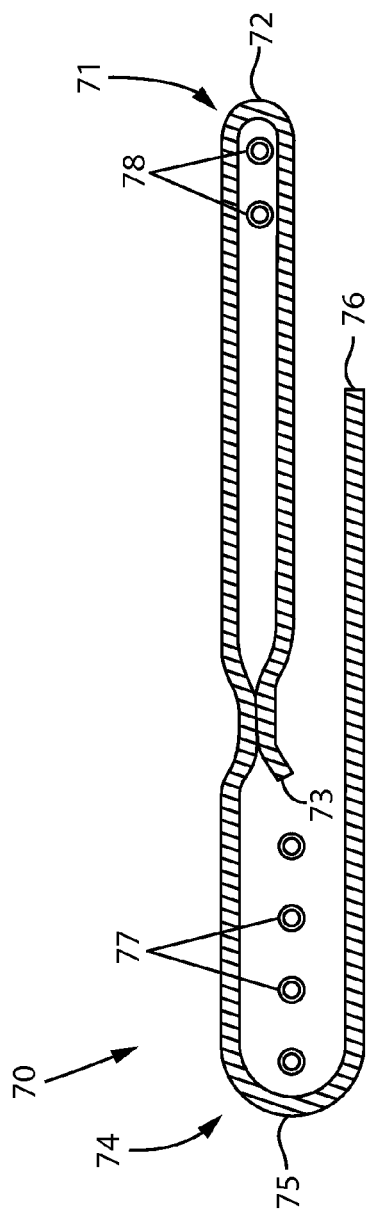
FIG. 2 is a schematic cross section view of an example of a folded outer leg cuff suitable in one embodiment of the invention.
Figure 3:
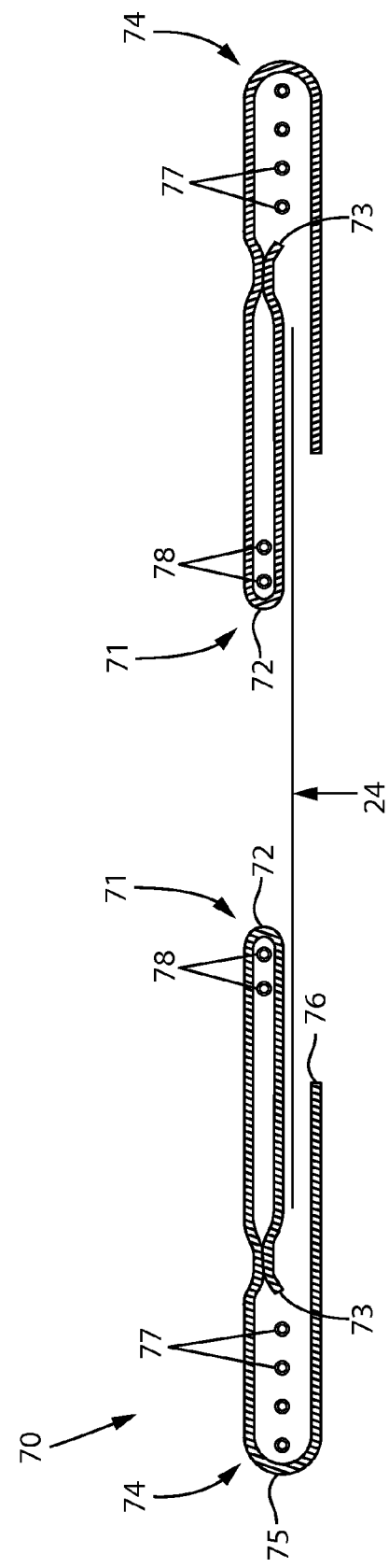
FIG. 3 is a schematic cross section view of an example of a folded outer leg cuff suitable in one embodiment of the invention.
Figure 4:
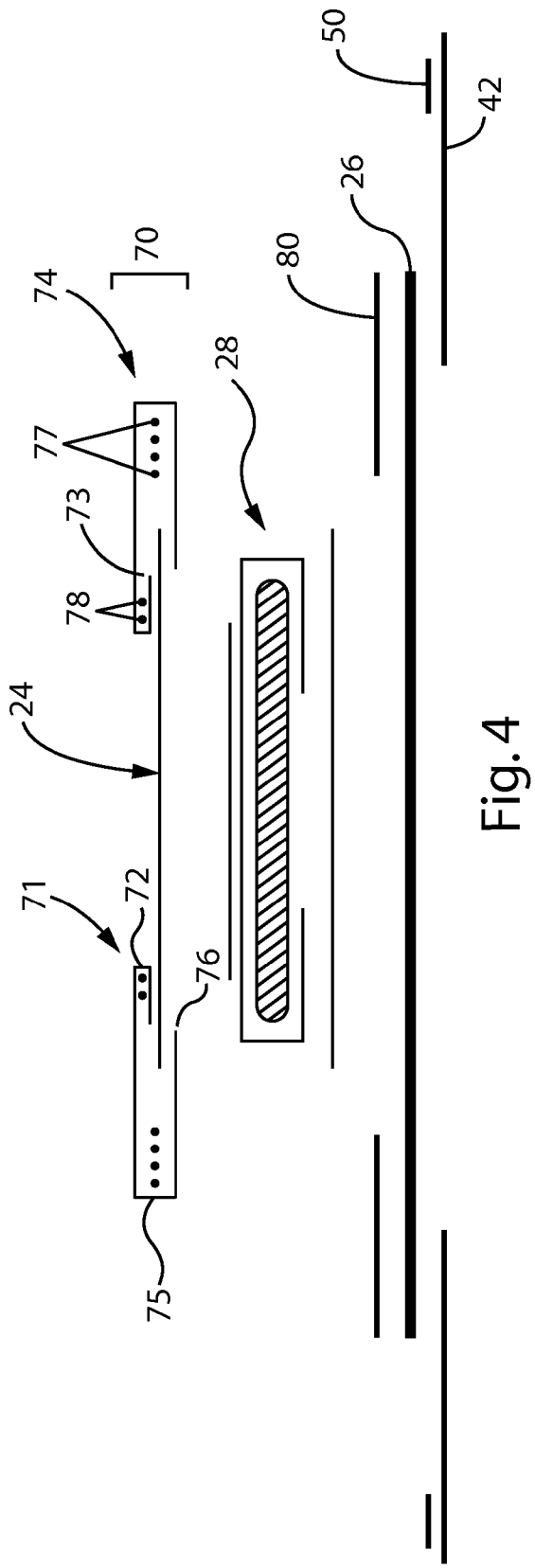
FIG. 4 is a schematic cross section view of an exemplary diaper.

The absorbent article 20 may include a leg gasketing system 70. FIGS. 2 and 3 depict schematic cross section views of exemplary leg gasketing systems. The leg gasketing system 70 may comprise an inner barrier leg cuff 71 comprising an inner cuff folded edge 72 and an inner cuff material edge 73. The leg gasketing system 70 may further comprise an outer cuff 74 comprising an outer cuff folded edge 75 and an outer cuff material edge 76.

In one embodiment, the leg gasketing system 70 comprises one web of material. An embodiment having one web of material may provide a cost advantage over embodiments having more than one web of material. Further, an embodiment having one web of material may have fewer leaks, as there are no holes created by bonding more than one web of material. Also, an embodiment having one web of material may be more aesthetically pleasing, as few mechanical bonds are visible.

In one embodiment, the leg gasketing system 70 has an inner barrier leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. In one embodiment, the web of material is folded laterally inward to form the outer cuff folded edge 75 and folded laterally outward to form the inner cuff folded edge 72. In one embodiment, the web of material is folded laterally inward to form the outer cuff folded edge 75 and folded laterally outward to form the inner barrier leg cuff. The barrier leg cuff material is folded laterally inward to form the inner cuff folded edge 72. The inner cuff comprises two layers of material and is folded laterally outward to form the inner barrier leg cuff and the barrier leg cuff fold 90, and laterally inward to form the inner cuff folded edge. In one embodiment, the leg gasketing system 70 extends from the first waist edge 36 to the second waist edge 38 and is joined to the topsheet 24 and/or backsheet 26 between the inner cuff folded edge 72 and the outer cuff folded edge 75 in the crotch region 37. In one embodiment, the outer cuff material edge 76 is disposed laterally inboard the inner cuff material edge 73. In one embodiment, the leg gasketing system 70 extends from the first waist edge 36 to the second waist edge 38 and is not joined to the topsheet 24. In one embodiment, the leg gasketing system is joined to the backsheet 26 between the inner cuff folded edge 72 and the outer cuff folded edge 75 in the crotch region 37. In one embodiment, the leg gasketing system is joined to the backsheet between the outer cuff material edge 76 and the topsheet 24.

In one embodiment, the outer leg cuff 74 and inner barrier leg cuff 71 are the same color. In one embodiment, the outer leg cuff 74 and inner barrier leg cuff 71 are different colors. In one embodiment, there is an additional printed cuff.

In one embodiment, the outer leg cuff 74 comprises elastic members 77 positioned in a lateral array between the outer cuff folded edge 75 and outer cuff material edge 76; the outer leg cuff 74 optionally comprises at least two elastic members 77, at least three elastic member 77, at least four elastic members 77, at least five elastic members 77, at least six elastic members 77. In one embodiment, the elastic members 77 may be disposed between the outer cuff folded edge 75 and the inner cuff material edge 73.

In one embodiment, the inner barrier leg cuff 71 comprises an array of elastic members 78 in the area of the inner cuff folded edge 72; the inner barrier leg cuff 71 optionally comprises at least one elastic member 78, at least two elastic members 78, at least three elastic members 78, at least four elastic members 78, at least five elastic members 78. In one embodiment, the elastic members 78 may be disposed between the inner cuff folded edge 72 and the outer cuff material edge 76.

In one embodiment, the outer leg cuff 74 comprises at least one more elastic member 77 than the inner leg cuff 71 elastic member 78. In one embodiment, the inner cuff material edge 73 is laterally outboard the outer cuff material edge 76.

In one embodiment, the elastic members 77 and 78 are spaced at least 2 mm apart from one edge to the other edge, optionally at least 3 mm apart; optionally at least 3.5 mm apart; optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. In one embodiment, the outermost elastic members 77 and 78 are less than about 2 mm from the outer cuff material edge 76 and inner cuff material edge 73; optionally less than about 1.5 mm, less than about 1 mm.

In one embodiment, the outer leg cuff 74 has four elastic members 77 that are about 4 mm apart. The outer leg cuff 74 may have four elastic members that are about 2 mm/7 mm/2 mm apart. The outer leg cuff 74 may have three elastic members 77 that are about 6 mm apart. The outer leg cuff 74 may have two elastic members that are about 12 mm apart. The outer leg cuff 74 may have two elastic members that are about 3 mm/6 mm/3 mm apart, as spaced from the outer cuff folded edge 75. In any embodiment, the elastic members may be about 2 mm from the outer cuff folded edge 75, optionally about 0 mm from the outer cuff folded edge 75.

The extensible properties of the leg gasketing system 70 are formed by the elastic members 77 in the outer leg cuff 74 and the elastic members 78 in the inner leg cuff 71 contracting to a relaxed length ($l_2$) that is shorter than the stretched length ($l_1$) ($l_2 < l_1$). This contraction creates a force ($F_1$) that is exerted on the aforementioned web of material that comprises the leg gasketing system 70. The force $F_1$ exerted by the contraction of elastic members 77 and 78 cause the web of material to have a reaction force ($F_2$) that results in the creation of gathers that contain the physical characteristics of waves—oscillations that have a wavelength, amplitude, and frequency within a given phase.

Wave Function: $y(t) = A \sin(wt + \Delta)$, where A=amplitude, w=frequency, Δ=phase or length (l)

The gathers created in the web of material in the leg gasketing system 70 can have different wave properties by varying the spacing of the elastic members 77 and 78 in the outer leg cuff 74 and inner leg cuff 71 respectively. Within a given contracted length ($l_2$) of web of material in the leg gasketing system 70, wider spacing of the elastic members 77 and 78 forms gathers that have a higher amplitude and lower frequency compared to gathers created by elastic members 77 and 78 with narrower spacing. This phenomenon occurs due to the force ($F_1$) created by the contraction to a relaxed length ($l_2$) of the elastic members 77 and 78 being exerted over a larger total area ($A_1$) for wider spacing of elastic members ($s_1$) and a smaller total area ($A_2$) for narrower spacing of elastic members ($s_2$) ($s_1 > s_2$). Wider spacing of elastic members 77 and 78 causes the force ($F_1$) to be exerted over a larger total area ($A_1$) resulting in less force to be exerted at any given point across the area of web of material in the leg gasketing system 70 comprised of the contracted elastic members 77 and 78. The reaction force ($F_2$) of the web of material in the leg gasketing system 70 for wider spacing is also less at any given point based on Newton's Third law of physics (forces acting in equal and opposite direction) resulting in gathers that have a wider wavelength (l), higher amplitude (A), and lower frequency (w) than gathers that are created by narrower spacing of elastic members 77 and 78 with a higher reaction force ($F_2$) resulting in higher force at any given point.

In one embodiment, the elastic members 77 and 78 are spaced apart from each other such that the outer leg cuff 74 and the inner leg cuff 71 are composed of differing tactile and aesthetic characteristics that create varying garment-like preferences. In one embodiment, the elastic members 77 and 78 can be strategically positioned to create regions of contraction that vary in amplitude and frequency. In one embodiment, the strategic positioning of the elastic members 77 and 78 can be spaced evenly or irregular to create contracted regions of uniform or changing amplitude and frequency in the outer leg cuff 74 and the inner leg cuff 71 such that a variety of garment-like preferences are achieved. In one embodiment, the elastic members 78 in the outer leg cuff 74 are strategically positioned to create contracted regions of smaller amplitude and higher frequency on the edges near the outer cuff folded edge 75 and the outer cuff material edge 76 and contracted region of higher amplitude and lower frequency in the center between the edges.

In one embodiment, the elastic members 77 are located between the inner cuff material edge 73 and the outer cuff folded edge 75. In one embodiment, the elastic members 78 are located between the outer cuff material edge 76 and the inner cuff folded edge 72. In one embodiment, an additional material may be located between the inner cuff material edge 73 and the outer cuff material edge 76; such material may include a topsheet 24; opacity strengthening patch 80; backsheet 28; core 26; or any other material optimally positioned in the design of the gasketing leg cuff 70. One such embodiment is shown in FIG. 3 wherein a topsheet 24 is positioned between the inner cuff material edge 73 and the outer cuff material edge 76. FIGS. 8 A-T depict cross section views of embodiments of the present invention. In one embodiment, the topsheet 24 is between the inner 71 and outer cuff 74 edges laterally.

In one embodiment, the leg gasketing system 70 has an inner barrier leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. The leg gasketing system may comprise a first material comprising the inner barrier leg cuff 71 and a second material comprising the outer cuff 74. The first and second material may overlap and be joined together along a longitudinal edge of each material by any suitable bonding means. In one embodiment, the web of material is folded laterally inward to form the outer cuff folded edge 75 and folded laterally outward to form the inner cuff folded edge 72. In one embodiment, the proximal edges of the outer cuff 74 are coterminous. In one embodiment, the proximal edges of the outer cuff 74 are spaced greater than about 2 mm apart; greater than about 4 mm; greater than about 6 mm; greater than about 10 mm apart. In one embodiment, the proximal material edges of the cuff are both bonded to the inner cuff. In one embodiment, only one of the proximal material edges of the outer cuff 74 are bonded to the inner cuff. In one embodiment, the proximal material edges of the outer cuff are held together with any suitable bonding means.

In one embodiment, the leg gasketing system is spaced laterally inward of the chassis edge by about 10 mm, optionally about 20 mm, optionally about 30 mm. In another embodiment, the laterally outboard edge of the chassis is defined by the lateral edge of the outer leg cuff. In another embodiment, the backsheet and polymeric film is spaced laterally inward of the outer cuff edge by about 10 mm; optionally about 20 mm; optionally about 30 mm; optionally about 40 mm.

In one embodiment, the laterally outboard edge of the leg gasketing system 70 is disposed laterally inboard at least a portion of the longitudinal edge of the article in at least one of the waist regions. Thus, in one embodiment, the front ears 40 and/or back ears 42 extend past the leg gasketing system 70.

In one embodiment, the height of the inner leg cuff 71 is at least about 30 mm, at least about 32 mm, at least about 35 mm, at least about 38 mm. In one embodiment, the height of the outer leg cuff 74 is at least about 23 mm, at least about 25 mm, at least about 27 mm, at least about 30 mm. The height of the inner cuff is measured from inner cuff folded edge to the first point of connection to a material beyond the inner cuff material edge. The outer cuff height is measured from the outer cuff folded edge to the first point of connection the inner cuff has to a material beyond the inner cuff material edge. Thus, the inner and outer cuffs are measured from their respective folded edges to the point where the inner cuff is connected to the first material beyond the inner cuff material edge.

One advantage of the leg gasketing system 70 of the present invention is that when a substantially liquid-impervious material is used in construction of the cuff, the polymeric film layer may be narrowed or not present at all, resulting in more cost effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

In one embodiment of the present invention, the backsheet polymeric film is less than about 50 mm wider than the absorbent core; optionally less than about 40 mm wider, less than about 30 mm wider. In one embodiment, the backsheet polymeric film is at least about 20 mm more narrow than the chassis width; optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width.

In one embodiment of the present invention, the leg cuff is joined to the topsheet and/or backsheet by a slot coated adhesive. In one embodiment, at least about 12 gsm of adhesive is applied; optionally at least about 15 gsm of adhesive is applied; optionally at least about 20 gsm of adhesive is applied; optionally, at least about 25 gsm of adhesive is applied; optionally at least about 40 gsm of adhesive is applied; optionally at least about 60 gsm of adhesive is applied. In one embodiment, the adhesive is at least about 1 mm wide; optionally at least about 3 mm wide; optionally at least about 7 mm wide. In one embodiment, the adhesive is at least about 2 mm inboard of the outboard lateral edge of the film; optionally at least 4 mm inboard of the outboard lateral edge of the film; optionally at least about 6 mm inboard of the outboard lateral edge of the film. In one embodiment, the leg cuff is joined to the topsheet and/or backsheet by two overlapping and redundant spiral adhesive sprays; optionally three overlapping and redundant spiral adhesive sprays.

In one embodiment of the present invention, an opacity strengthening patch 80 may be included. The opacity strengthening patch 80 is an additional layer of material. The opacity strengthening patch 80 may be connected to the leg gasketing system 70, the polymeric film layer, or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the leg gasketing system 70 or the polymeric film layer. The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis where strength and opacity is desirable. Materials suitable to act as the opacity strengthening patch include materials having a basis weight of at least about 10 gsm, at least about 15 gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

In one embodiment, the opacity strengthening patch is discrete and is located in the front and back waist regions of the article. In one embodiment, the opacity strengthening patch is about 70 mm long in the front, optionally about 90 mm long in the front; optionally about 120 mm long in the front. In one embodiment, the opacity strengthening patch is about 70 mm long in the back, optionally about 100 mm long in the back, optionally about 140 mm long in the back. In one embodiment, the opacity strengthening patch is continuous and spans the entire length of the product.

In one embodiment, the opacity strengthening patch has a hunter color opacity of greater than about 15%, optionally greater than about 25%, optionally greater than about 40%, optionally greater than 60%.

In one embodiment the opacity strengthening patch is laterally outboard of the polymeric film layer. In one embodiment, the opacity strengthening patch overlaps the polymeric film layer in the lateral direction such that it can be affixed to the polymeric film in order to transmit laterally directed application and wearing forces from the opacity strengthening patch to the polymeric film layer. Any suitable bonding means known in the art may be used to affix the opacity strengthening patch to the polymeric film layer. In one embodiment, the opacity strengthening patch overlaps the polymeric film layer by about 5 mm, optionally about 10 mm, optionally about 15 mm, optionally about 20 mm, optionally less than about 30 mm.

In one embodiment, there is a lateral gap between the opacity strengthening patch and the polymeric film layer and the opacity strengthening patch is affixed by any suitable bonding means to the leg gasketing system, and the leg gasketing system is affixed to the polymeric film layer by any suitable bonding means such that application and wearing loads can transmit from the opacity strengthening patch to the gasketing system and then from the gasketing system to the polymeric film layer. In this embodiment, the gap is preferably less than 30 mm, more preferably less than 20 mm, more preferably less than 10 mm.

In one embodiment, there is a lateral gap between the opacity strengthening patch and the polymeric film layer; the opacity strengthening patch may be affixed by any suitable bonding means to the leg gasketing system and the body facing and garment facing sides of the leg gasketing system may be affixed together by any suitable bonding means so that the loads from the opacity strengthening patch are shared by both layers of the leg gasketing system. The leg gasketing system may be affixed to the polymeric film layer by any suitable bonding means such that application and wearing loads can transmit from the opacity strengthening patch to the leg gasketing system and then from the leg gasketing system to the polymeric film layer.

In one embodiment, the opacity strengthening patch overlaps the leg gasketing system in the lateral direction such that it can be affixed securely to the opacity strengthening patch layer by any suitable bonding means as a way to transmit application and wearing forces from the opacity strengthening patch to the leg gasketing system. In this embodiment, the opacity strengthening patch may overlap the leg gasketing system by about 5 mm, optionally about 10 mm, optionally less than about 15 mm, optionally less than about 25 mm.

In one embodiment the leg gasketing system has about the same lateral tensile strength properties as the opacity strengthening patch. In one embodiment the combined properties of the leg gasketing system and the backsheet nonwoven outer cover has about the same lateral tensile strength as the opacity strengthening patch. In another embodiment the outer cover nonwoven has very low lateral strength between about 0% and about 10% engineering strain. In one embodiment, the outer cover nonwoven may exhibit the following tensile properties: at 10% engineering strain for a 1 inch wide sample, 0.4N.

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example.

The leg gasketing cuff 70 may comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

In some embodiments, the use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. N-fibers are further discussed in WO 2005/095700 and U.S. patent application Ser. No. 13/024,844.

In one embodiment, the inner leg cuff 71 web of material has a hydrostatic head of greater than about 2 mbar, greater than about 3 mbar, greater than about 4 mbar. In one embodiment, the outer leg cuff 74 web of material has a hydrostatic head of less than about 200 mbar, less than about 100 mbar, less than about 75 mbar, less than about 50 mbar, less than about 25 mbar, less than about 15 mbar.

In one embodiment, the folded outer leg cuff web of material has a basis weight of 10 gsm; optionally 13 gsm; optionally 15 gsm; optionally 18 gsm.

In one embodiment, the inner leg cuff 71 web of material has an opacity of from about 15% to about 50% hunter opacity; optionally from about 20% to about 45% hunter opacity. In one embodiment, the outer leg cuff 74 web of material has an opacity of from about 45% to about 75% hunter opacity; optionally from about 50% to about 70% hunter opacity; optionally less than about 75% hunter opacity; optionally less than about 70% hunter opacity.

In one embodiment, the inner leg cuff 71 web of material has an air permeability of less than about 50 $m^3/m^2/min$; optionally less than about 45 $m^3/m^2/min$. In one embodiment, the outer leg cuff 74 web of material has an air permeability of greater than about 5 $m^3/m^2/min$; optionally greater than about 10 $m^3/m^2/min$; optionally greater than about 15 $m^3/m^2/min$; optionally greater than about 20 $m^3/m^2/min$.

In one embodiment, the inner leg cuff 71 web of material has a WVTR of less than about 5500 $g/m^2/24$ hrs; optionally less than about 5400 $g/m^2/24$ hrs. In one embodiment, the outer leg cuff 74 web of material has a WVTR of greater than about 4250 $g/m^2/24$ hrs; optionally greater than about 4500 $g/m^2/24$ hrs; optionally greater than about 5000 $g/m^2/24$ hrs; optionally greater than about 5250 $g/m^2/24$ hrs; optionally greater than about 5500 $g/m^2/24$ hrs.

The gasketing cuffs 70 may be substantially inelastic or may be elastically extensible to dynamically fit at the wearer's leg. The gasketing cuff 70 may be formed by one or more elastic members 77 and 78 (such as elastic strands) operatively joined to the topsheet 24, backsheet 26, or any other suitable substrate used in the formation of the absorbent article 20. Suitable gasketing cuff construction is further described in U.S. Pat. No. 3,860,003

The inner barrier cuff 71 may span the entire longitudinal length of the absorbent article 20. The inner barrier cuff 71 may be formed by a flap and an elastic member 78 (such as elastic strands). The inner barrier cuff 71 may be a continuous extension of any of the existing materials or elements that form the absorbent article 20.

The inner barrier cuff 71 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap may comprise a nonwoven web such as spunbond webs, meltblown webs, carded webs, and combinations thereof (e.g., spunbond-meltblown composites and variants). Laminates of the aforementioned substrates may also be used to form the flap. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having inner barrier cuffs and suitable construction of such barrier cuffs may be found in U.S. Pat. Nos. 4,808,178 and 4,909,803. The elastic member 78 may span the longitudinal length of the inner barrier cuff 71. In other embodiments, the elastic member 78 may span at least the longitudinal length of the inner barrier cuff 71 within the crotch region 37. It is desirable that the elastic member 78 exhibits sufficient elasticity such that the inner barrier cuff 71 remains in contact with the wearer during normal wear, thereby enhancing the barrier properties of the inner barrier cuff 71. The elastic member 78 may be connected to the flap at opposing longitudinal ends. In certain embodiments, the flap may be folded over onto itself so as to encircle the elastic member 78.

The inner barrier cuff 71 and/or outer cuff 74 may be treated, in full or in part, with a lotion, as described above with regard to topsheets, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning Mich., Salzburg as supplier code 0010024820.

Figure 5:
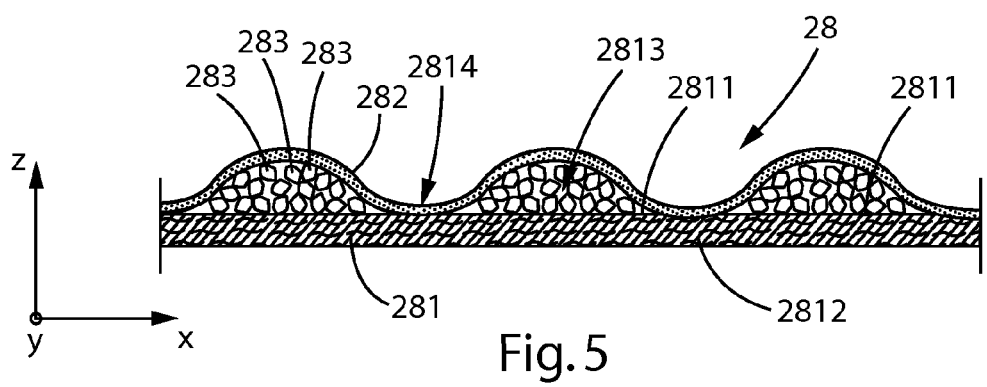
FIG. 5 is a schematic cross section view of an example of an absorbent core suitable in one embodiment of the invention.
Figure 6:
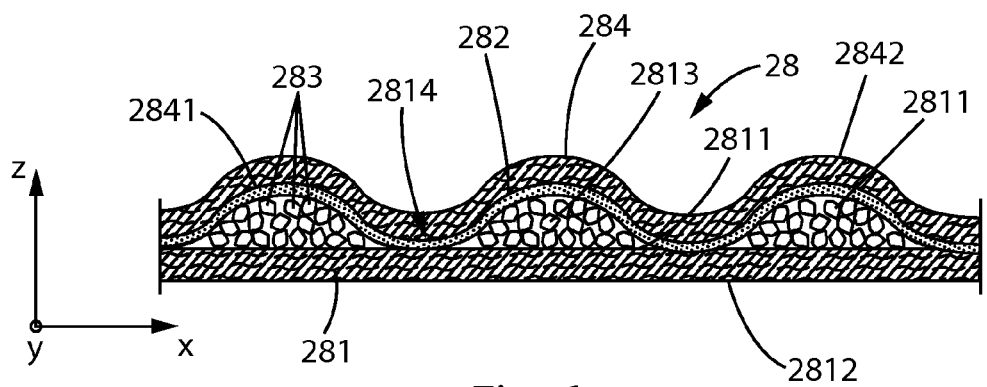
FIG. 6 is a schematic cross section view of another example of an absorbent core suitable in one embodiment of the invention.
Figure 7:
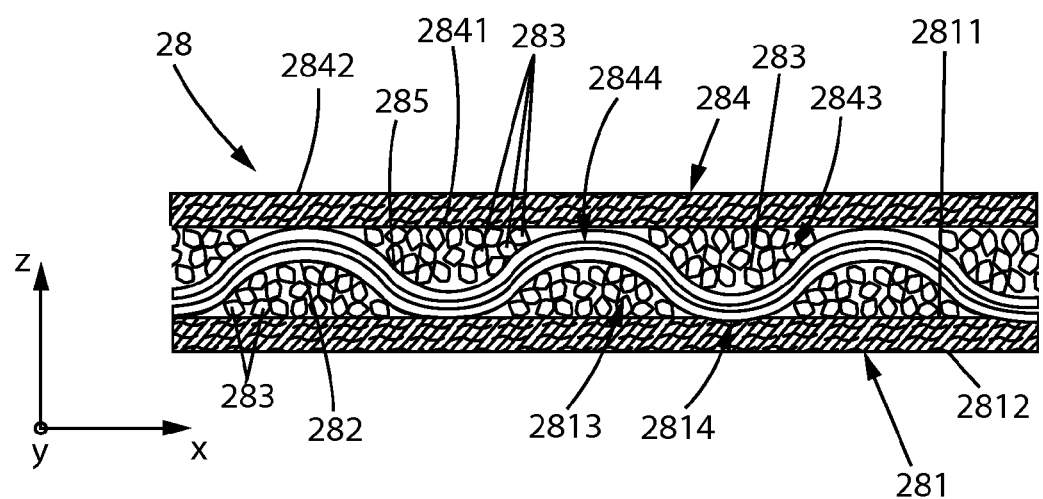
FIG. 7 is a schematic cross section view of another example of an absorbent core suitable in one embodiment of the invention.
Figure 8Q:
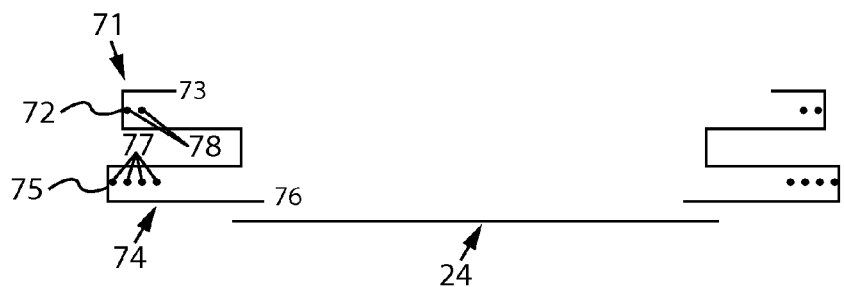
FIGS. 8 A-T include schematic cross section views of embodiments a folded outer leg cuff suitable in the invention.
Figure 8R:
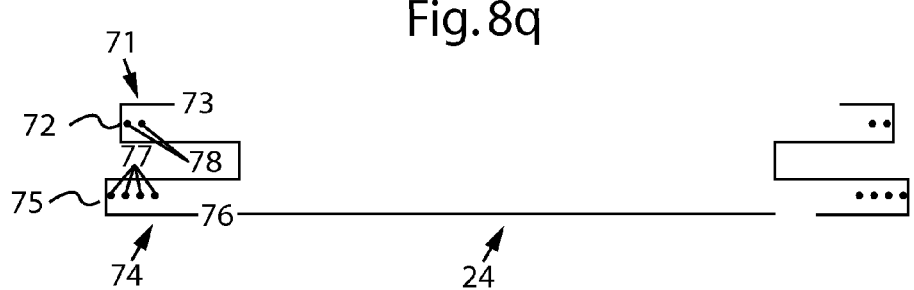
Figure 8S:
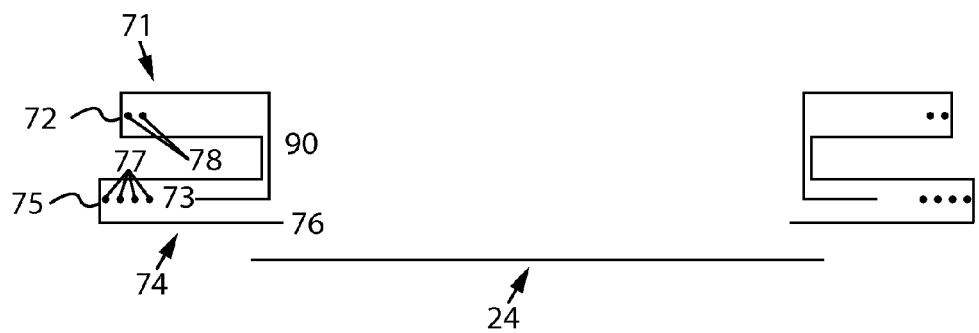
Figure 8T:
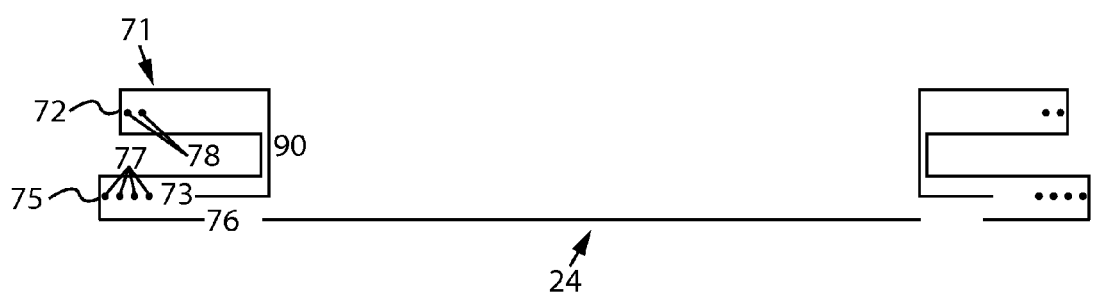

In one embodiment, an absorbent article includes an absorbent core 28 that is substantially cellulose free. Cross-sectional views of examples of suitable absorbent cores are schematically represented in FIGS. 5-7. The absorbent core 28 is the element of the absorbent article whose primary function is to absorb and retain liquid body exudates. Additional elements may be added between the topsheet and the absorbent core of an absorbent article to facilitate the acquisition and the distribution of body exudates. Such elements may include, for example, an acquisition layer and/or a distribution layer as it is well known in the art. The acquisition and/or distribution layers may themselves be substantially cellulose free (for example made entirely of a nonwoven material) or include a significant amount of cellulosic material. Although an absorbent core generally includes absorbent materials in particulate form having a high retention capacity such as, for example absorbent polymers, these materials do not need to be present along the entire length of the absorbent core. It may be advantageous to provide an absorbent core with a greater amount of absorbent material in the crotch area and/or the first waist region in comparison to the second waist region which may include only a little amount, if any, of absorbent polymers. In one embodiment, an absorbent core 28 comprises first and second layers of material 281, 282 and an absorbent material 283 disposed between the first and second layers 281, 282. In one embodiment the first and second layers of material can be a fibrous material chosen from at least one of a nonwoven fibrous web, a woven fibrous web and a layer of thermoplastic adhesive material. Although the first and second layers can be made of a same material, in one embodiment, the first layer 281 is a nonwoven fibrous web and the second layer 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblow fibers. In one embodiment, the nonwoven web 281 can be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer 281 comprises a first surface 2811 and a second surface 2812 and at least regions 2813 of the first surface are in direct facial relationship with a significant amount of absorbent material 283. In one embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material. By "direct facial relationship with a significant amount of absorbent material" it is meant that some absorbent material is deposited on top of the regions 2813 at a basis weight of at least 100 g/m$^2$, at least 250 g/m$^2$ or even at least 500 g/m$^2$. The pattern may include regions that all have the same shape and dimensions (i.e. projected surface area and/or height). In the alternative the pattern may include regions that have different shape or dimensions to form a gradient of regions. At least some of the regions 2813 can have a projected surface area of between 1 cm$^2$ and 150 cm$^2$ or even between 5 cm$^2$ and 100 cm$^2$. By "facial relationship with an insignificant amount of absorbent material" it is meant that some absorbent material may be deposited on top of the regions 2814 at a basis weight of less than 100 g/m$^2$, less than 50 g/m$^2$ or even substantially no absorbent material. At least some of the regions 2814 can have a projected surface area of between 1 cm$^2$ and 150 cm$^2$ or even between 5 cm$^2$ and 100 cm$^2$. The aggregate projected surface area of all the regions 2813 can represent between 10% and 90% or even between 25% and 75% of the total projected surface area of the first surface 2811 of the first layer 281. In one embodiment, the second layer 282 is a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20 to about 40% by weight. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In exemplary embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0 to about 15%.

The thermoplastic adhesive material 282 can be disposed substantially uniformly within the absorbent material 283. In the alternative, the thermoplastic adhesive material 282 can be provided as a fibrous layer disposed on top of the absorbent material 283 and the regions 2814 of the first surface 2811 that are in facial relationship with only an insignificant amount of absorbent material. In one embodiment, a thermoplastic adhesive material is applied at an amount of between 1 and 20 g/m$^2$, between 1 and 15 g/m$^2$ or even between 2 and 8 g/m$^2$. The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In one embodiment, the absorbent core 28 may further comprise a second layer of a nonwoven fibrous material 284. This second layer may be provided of the same material as the nonwoven fibrous layer 281, or in the alternative may be provided from a different material. It may be advantageous for the first and second nonwoven fibrous layers 281, 284 to be different in order to provide these layers with different functionalities. In one embodiment, the surface energy of the first nonwoven layer can be different than the surface energy of the second nonwoven layer. In one embodiment, the surface energy of the second nonwoven layer is greater than the surface energy of the first nonwoven layer. Among over benefits, it is believed that when the surface energy of the second nonwoven layer is greater than the surface energy of the first nonwoven layer, liquids such as urine will be able to penetrate the second nonwoven layer more easily in order to reach and be retained by the absorbent material while at the same time reducing the chances that the liquid may penetrate and go through the first layer. This may be particularly advantageous when the first nonwoven layer is disposed against the backsheet of an absorbent article. The different surface energies of each layer may be obtained, for example, by applying a different amount of an agent such as a surfactant to the second nonwoven layer than the amount of surfactant (if any) applied to the first nonwoven layer. This may also be achieved by applying a different type of surfactant to the second nonwoven layer than the surfactant applied to the first nonwoven layer. This may still be achieved by applying a material to the first nonwoven layer that lowers its surface energy. In addition to having different surface energies, or in the alternative, the first and second nonwoven fibrous layers 281, 284 may also be different structurally. In one embodiment, the first nonwoven layer 281 may include different layers of fibers than the second nonwoven layer. For example, the second nonwoven layer 284 may only include one or more layers of spunbond fibers whereas the first nonwoven layer 281 includes one or more layers of spunbond fibers and one or more layers of meltblown fibers. In another embodiment, both nonwoven fibrous layers 281, 284 may include one or more layers of spunbond fibers and one or more layers of meltblow fibers but the first and second layers 281, 284 differ in terms of at least one of the chemical composition of the fibers used to form the nonwoven material, the denier of the fibers and/or the basis weight of the nonwoven material. In addition to or in the alternative than the above the first and second nonwoven layers 281, 284 may also differ in terms of at least one of their respective hydrohead values, their respective porosity, their respective Frazier permeability and their respective tensile properties. The second nonwoven layer 284 may applied directly on top of the first nonwoven layer 281, the absorbent material 283 and the thermoplastic adhesive material 282. As a result, the first and second nonwoven layers 281 and 284 further encapsulate and immobilize the absorbent material 283.

The regions 2813 may have any suitable shape in the x-y dimension of the absorbent core. In one embodiment, the regions 2813 form a pattern of disc that are spread on the first surface of the first web 281. In one embodiment, the regions 2813 form a pattern of longitudinal "strips" that extend continuously along the longitudinal axis of the absorbent core (i.e. along the y dimension). In an alternative embodiment, these strips may be are arranged to form an angle of at between 10 and 90 degrees, between 20 and 80 degrees, between 30 and 60 degrees, or even 45 degrees relative to the longitudinal axis of the absorbent article.

In one embodiment, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In one embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In one embodiment, the pattern of absorbent material present on the second nonwoven layer 284 may be the same as the pattern of absorbent material present on the first nonwoven layer 281. In an other embodiment, the patterns of absorbent material that are present on the first and second nonwoven layers are different in terms of at least one of the shape of the regions, the projected surface areas of the regions, the amount of absorbent material present on the regions and the type of absorbent material present on the regions. It is believed that when the patterns of absorbent material that are present on the first and second nonwoven layers are different, each layer/absorbent composite may have different functionalities such as for example, different absorbent capacities and/or different acquisition rates of liquids. It can be beneficial for example to provide an absorbent core with a structure where the second pattern formed by the regions 2843 of absorbent material (i.e. on the second nonwoven layer 284) exhibits a slower acquisition rate than the first pattern of regions 2813 of absorbent material in order to allow liquids, such as urine, to reach and be absorbed by the absorbent material deposited on the first nonwoven layer 281 before expansion of the absorbent material in the regions 2843. Such a structure avoids any significant gel blocking by the absorbent material present in the regions 2843. It can also be advantageous to apply the second layer/absorbent material/thermoplastic adhesive material composite in such a way that at least some of or even all of the regions 2813 of the first nonwoven layer 281 that are in direct facial relationship with a significant amount of absorbent material are also in substantial facial relationship with corresponding regions 2844 of the second web 284, which are in facial relationship with an insignificant amount of absorbent material.

The absorbent core 28 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01). In one embodiment, the absorbent material 283 is absorbent polymer material which is in particulate form so as to be flowable in the dry state.

As previously discussed, the absorbent material 283 present in the absorbent cores 28 of an absorbent article, does not need to be present along the entire length of the absorbent core. In one embodiment, the back section 328 of an absorbent article includes an insignificant amount of absorbent material 283 whereas at least the middle 228 and/or the front section 128 include a greater amount of absorbent material than the back section 328. For example, the back section 328 may include less than 5 grams, or less than 3 grams, less than 2 grams or even less than 1 g of a particulate absorbent polymer material. The middle section 228 may include at least 5 grams, or at least 8 grams, or even at least 10 grams of a particulate absorbent polymer material. The front section 128 may include between 1 and 10 grams, or between 2 and 8 grams of a particulate absorbent polymer material.

EXAMPLES

| Product | Lot No. | Opacity % Outer Cuff | Opacity % Inner Cuff | Air Permeability $m^3/m^2/min$ Outer Cuff | Air Permeability $m^3/m^2/min$ Inner Cuff | WVTR $g/m^2/24\ hrs$ Outer Cuff | WVTR $g/m^2/24\ hrs$ Inner Cuff |
|---|---|---|---|---|---|---|---|
| Prototype N-Fiber | NA | 58.7 ± 2.2 | 37.6 ± 3.2 | 26.8 ± 5.6 | 36.9 ± 4.6 | 5905 ± 129 | 5224 ± 87 |
| Prototype SMS | NA | 65.8 ± 1.8 | 39.0 ± 1.0 | 65.6 ± 11.5 | 38.5 ± 3.8 | 5748 ± 276 | 5193 ± 145 |
| Pampers BabyDry | 0089U011390422 | 80.1 ± 0.4 | 38.8 ± 3.8 | 2.1 ± 1.0 | 56.1 ± 6.3 | 4063 ± 67 | 5252 ± 157 |
| Luvs | 1047U011390518 | 85.3 ± 1.2 | 36.4 ± 3.4 | 3.1 ± 1.9 | 90.2 ± 9.3 | 304 ± 144 | 5244 ± 26 |
| Huggies Little Movers | BI006912B | 80.1 ± 1.0 | 45.4 ± 4.2 | 2.6 ± 0.4 | 45.0 ± 15.7 | 3673 ± 190 | 5581 ± 90 |

| | | | | | | |
|---|---|---|---|---|---|---|
| Huggies Supreme | NM1275U1F0755 | 72.7 ± 2.2 | 53.6 ± 2.3 | 4.4 ± 1.1 | 145.2 ± 23.2 | 375 ± 77 | 5688 ± 85 |

| | | Hydrohead mbar | | 32 dyne Strikethrough sec | |
|---|---|---|---|---|---|
| Product | Lot No. | Outer Cuff | Inner Cuff | Outer Cuff | Inner Cuff |
| Prototype N-Fiber | NA | 16.8 ± 2.1 | 12.3 ± 1.3 | 21.0 ± 3.5 | 9.2 ± 1.5 |
| Prototype SMS | NA | 16.3 ± 1.8 | 10.0 ± 1.7 | 15.6 ± 1.9 | 7.6 ± 1.4 |
| Pampers BabyDry | 0089U011390422 | >200 | 6.7 ± 0.8 | >100 | 10.1 ± 0.5 |
| Luvs | 1047U011390518 | >200 | 6.5 ± 1.0 | >100 | 11.8 ± 1.4 |
| Huggies Little Movers | BI006912B | >200 | 8.3 ± 1.3 | >100 | 14.3 ± 3.5 |
| Huggies Supreme | NM1275U1F0755 | >200 | 9.2 ± 1.8 | >100 | 14.6 ± 3.1 |

Results are expressed as the average ± one standard deviation
Prototype N-Fiber is a 13 gsm SMNS available from Polymer Group Inc
Prototype SMS is a 15 gsm SMS (Spunbonded-Meltblown-Spunbonded) nonwoven available from Fibertex under the Comfort Line Test Methods
Opacity Method Opacity is measured using a 0° illumination/45° detection, circumferential optical geometry, spectrophotometer with a computer interface such as the HunterLab LabScan XE running Universal Software (available from Hunter Associates Laboratory Inc., Reston, Va.) or equivalent instrument. Instrument calibration and measurements are made using the standard white and black calibration plates provided by the vendor. All testing is performed in a room maintained at 23±2° C. and 50±2% relative humidity.

The spectrophotometer is configured for the XYZ color scale, D65 illuminant, 10° standard observer, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

$$\text{Opacity} = (Y\text{value}_{(black\ backing)}/Y\text{value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs and the outer cuffs are calculated and report separately, each to the nearest 0.01%.

Water Vapor Transmission Rate Method

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2 C.° and 50%±2% relative humidity.

Articles are preconditioned at 23° C.±2 C.° and 50%±2% relative humidity for two hours prior to testing. The article stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens from the cuffs on the right side of the article are prepared.

Glass straight walled, cylindrical vials, 95 mm tall with a 17.8 mm internal diameter at the opening are used as WVTR test vials. Each test vial is filled with distilled water accurately to a level 25.0 mm±0.1 mm from the upper lip of the vial's opening. The specimen is placed, inner-facing surface of the cuff downward, over the vial's opening. The specimen is gently pulled taut and secured around the vial's circumference with an elastic band. The specimen is further sealed by wrapping Teflon tape around the vial's circumference. A preferred Teflon tape is a thread sealant tape 0.25" wide available from McMaster Can (cat. No. 4591K11) or equivalent. The Teflon tape is applied up to the top edge of the vial but should not cover any portion of the vial's opening. The mass of the vial assembly (vial+specimen+sealing tape) is weighed to the nearest 0.0001 gram. This is the starting mass.

The vial assemblies are placed upright in a mechanical convection oven (e.g. Lindberg/BlueM oven available from ThermoScientific or equivalent) maintained at 38±1° C. for 24 hours, taking care to avoid contact between the water in the vials and the specimens. After 24 hours has elapsed, the vial assemblies are removed from the oven and allowed to come to room temperature. The mass of each vial assembly is measured to the nearest 0.0001 gram. This is the final mass.

The WVTR is calculated using the following equation:

$$\text{WVTR (g/m}^2/24 \text{ hrs)} = ([\text{starting mass (g)} - \text{final mass (g)}]/\text{surface area (m}^2))/24 \text{ hrs}$$

Specimens from five identical articles (10 inner cuff (5 left and 5 right) and 10 outer cuff (5 left and 5 right)) are analyzed and their WVTR results recorded. The average WVTR for the inner cuffs and the outer cuffs are each reported separately to the nearest 1 g/m$^2$/24 hrs.

Air Permeability Test

Air permeability is tested using a TexTest FX3300 Air Permeability Tester (available from Advanced Testing Instruments, Greer, S.C.) with a custom made 1 cm$^2$ circular aperture (also available from Advanced Testing Instruments) or equivalent instrument. The instrument is calibrated according to the manufacturer's procedures. All testing is performed in a room maintained at 23° C.±2 C.° and 50%±2% relative humidity.

The articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is typically set for 125 Pa and for cuffs containing films typically 2125 Pa is used. The sample ring is closed and the measuring range is adjusted until the range indicator shows green to indicate that the measurement is within the accepted limits of the instrument. The air permeability is recorded to the nearest 0.1 m$^3$/m$^2$/min.

Hydrostatic Head Test

Hydrostatic head is tested using a TexTest FX3000 Hydrostatic Head Tester (available from Advanced Testing Instruments, Greer, S.C.) with a custom made 1.5 cm$^2$ circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2 C.° and about 50%±2% relative humidity.

Precondition the articles at about 23° C.±2 C.° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs and the outer cuffs and report each to the nearest 0.1 mbar.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad.

For this test, the reference absorbent pad is 5 plies of Ahlstrom grade 989 filter paper (10 cm×10 cm) and the test fluid is a 32 mN/m low surface tension fluid.

This test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria)

and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strikethrough time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

All testing is performed in a room maintained at about 23° C.±2 C.° and about 50%±2% relative humidity. The Ahlstrom filter paper and test articles are conditioned in this controlled environment for 24 hours and 2 hours before testing.

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Precondition the test articles at about 23° C.±2 C.° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the strike through plate. The specimen should completely cover the port with the surface corresponding to the body-facing surface of the cuff directed toward the port. Gently extend the specimen taut in its longitudinal direction so that the cuff lies flat against the upper test plate. Adhesive tape is applied to secure the cuff to the test plate in its extended state for testing. Tape should not cover any portion of the measurement port.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for three articles. Average the six values and report as the 32 mN/m low surface tension strikethrough time to the nearest 0.1 seconds.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge, the disposable absorbent article comprising:
1.) a topsheet;
2.) a backsheet;
3.) an absorbent core disposed between the topsheet and the backsheet; and
4.) a leg gasketing system, wherein the leg gasketing system comprises an inner cuff and an outer cuff; wherein the inner cuff comprises an inner cuff folded edge and an inner cuff material edge; wherein the outer cuff comprises an outer cuff folded edge and an outer cuff material edge such that the web of material is folded laterally inward to form the outer cuff folded edge and folded laterally outward to form the inner cuff folded edge, wherein the leg gasketing system extends from the first waist edge to the second waist edge and is joined to the topsheet and/or backsheet between the inner cuff folded edge and the outer cuff folded edge in the crotch region, wherein the inner cuff has an air permeability of less than about 50 m³/m²/min and the outer cuff has an air permeability of greater than about 5 m³/m²/min.

2. The disposable absorbent article of claim 1, wherein the leg gasketing system does not comprise a polymeric film.

3. The disposable absorbent article of claim 1, wherein the leg gasketing system comprises an N-fiber material.

4. The disposable absorbent article of claim 1, wherein the inner cuff has a hydrostatic head of greater than about 2 mbar and the outer cuff has a hydrostatic head of less than about 200 mbar.

5. The disposable absorbent article of claim 1, wherein the inner cuff has a Low Surface Tension Fluid Strikethrough Time of greater than about 15 seconds and less than about 200 seconds and the outer cuff has a Low Surface Tension Fluid Strikethrough Time of greater than about 20 seconds and less than about 200 seconds.

6. The disposable absorbent article of claim 1, wherein the inner cuff has an opacity of from about 15% to about 50% hunter opacity and the outer cuff has an opacity of from about 45% to about 75% hunter opacity.

7. The disposable absorbent article of claim 1, wherein the leg gasketing system comprises at least two elastic members on the inner cuff.

8. The disposable absorbent article of claim 1, wherein the leg gasketing system comprises at least three elastic members on the outer cuff.

9. The disposable absorbent article of claim 1, wherein the leg gasketing system is comprised of one web of material.

10. The disposable absorbent article of claim 1, wherein the outer cuff material edge is disposed laterally inboard the inner cuff material edge.

11. The disposable absorbent article of claim 1, wherein elastic members are located between the inner cuff material edge and the outer cuff folded edge.

12. The disposable absorbent article of claim 1, wherein elastic members are located between the inner cuff folded edge and outer cuff material edge.

13. The disposable absorbent article of claim 1, wherein the outer cuff folded edge is located laterally outboard of a chassis edge in the crotch region.

14. The disposable absorbent article of claim 1, wherein the topsheet is not attached to the leg gasketing system.

15. The disposable absorbent article of claim 1, wherein the backsheet is attached to the leg gasketing system between the outer cuff material edge and the topsheet.

16. The disposable absorbent article 1, wherein the inner cuff is two layers.

17. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge, the disposable absorbent article comprising:
 1.) a topsheet;
 2.) a backsheet;
 3.) an absorbent core disposed between the topsheet and the backsheet; and
 4.) a leg gasketing system, wherein the leg gasketing system comprises an inner cuff and an outer cuff; wherein the inner cuff comprises an inner cuff folded edge and an inner cuff material edge; wherein the outer cuff comprises an outer cuff folded edge and an outer cuff material edge such that the web of material is folded laterally inward to form the outer cuff folded edge and folded laterally outward to form the inner cuff folded edge,
wherein the leg gasketing system extends from the first waist edge to the second waist edge and is joined to the topsheet and/or backsheet between the inner cuff folded edge and the outer cuff folded edge in the crotch region,
wherein the inner cuff has a WVTR of less than about 5500 g/m²/24 hrs and the outer cuff has a WVTR of greater than about 4250 g/m²/24 hrs.

18. The disposable absorbent article of claim 17, wherein the leg gasketing system does not comprise a polymeric film.

19. The disposable absorbent article of claim 17, wherein the leg gasketing system comprises an N-fiber material.

20. The disposable absorbent article of claim 17, wherein the inner cuff has a hydrostatic head of greater than about 2 mbar and the outer cuff has a hydrostatic head of less than about 200 mbar.

21. The disposable absorbent article of claim 17, wherein the inner cuff has a Low Surface Tension Fluid Strikethrough Time of greater than about 15 seconds and less than about 200 seconds and the outer cuff has a Low Surface Tension Fluid Strikethrough Time of greater than about 20 seconds and less than about 200 seconds.

22. The disposable absorbent article of claim 17, wherein the inner cuff has an opacity of from about 15% to about 50% hunter opacity and the outer cuff has an opacity of from about 45% to about 75% hunter opacity.

23. The disposable absorbent article of claim 17, wherein the leg gasketing system comprises at least two elastic members on the inner cuff.

24. The disposable absorbent article of claim 17, wherein the leg gasketing system comprises at least three elastic members on the outer cuff.

25. The disposable absorbent article of claim 17, wherein the leg gasketing system is comprised of one web of material.

26. The disposable absorbent article of claim 17, wherein the outer cuff material edge is disposed laterally inboard the inner cuff material edge.

27. The disposable absorbent article of claim 17, wherein elastic members are located between the inner cuff material edge and the outer cuff folded edge.

28. The disposable absorbent article of claim 17, wherein elastic members are located between the inner cuff folded edge and outer cuff material edge.

29. The disposable absorbent article of claim 17, wherein the outer cuff folded edge is located laterally outboard of a chassis edge in the crotch region.

30. The disposable absorbent article of claim 17, wherein the topsheet is not attached to the leg gasketing system.

31. The disposable absorbent article of claim 17, wherein the backsheet is attached to the leg gasketing system between the outer cuff material edge and the topsheet.

32. The disposable absorbent article 17, wherein the inner cuff is two layers.

* * * * *

UNITED STATES PATENT AND TRADEMARK OFFICE
CERTIFICATE OF CORRECTION

PATENT NO.        : 8,939,957 B2  
APPLICATION NO.   : 13/457521  
DATED             : January 27, 2015  
INVENTOR(S)       : Jeromy Thomas Raycheck et al.

Page 1 of 1

It is certified that error appears in the above-identified patent and that said Letters Patent is hereby corrected as shown below:

Title Page, item (57)

Abstract – Line 10

Delete "cuff material edge" and add --cuff folded edge--

In the Specification

Column 2, Line 45

Delete "cuff material edge" and add --cuff folded edge--

Column 2, Line 46

Delete "waist edge may be" and add --waist edge and may be--

Signed and Sealed this  
Twenty-third Day of February, 2016

Michelle K. Lee  
*Director of the United States Patent and Trademark Office*